(12) United States Patent
Köklü

(10) Patent No.: US 9,237,940 B2
(45) Date of Patent: Jan. 19, 2016

(54) ORTHODONTIC APPARATUS

(76) Inventor: Saduman Oguzhan Köklü, Schwelm (DE)

( * ) Notice: Subject to any disclaimer, the term of this patent is extended or adjusted under 35 U.S.C. 154(b) by 0 days.

(21) Appl. No.: 13/996,244

(22) PCT Filed: Dec. 13, 2011

(86) PCT No.: PCT/EP2011/072644
§ 371 (c)(1),
(2), (4) Date: Jul. 10, 2013

(87) PCT Pub. No.: WO2012/084611
PCT Pub. Date: Jun. 28, 2012

(65) Prior Publication Data
US 2013/0295514 A1    Nov. 7, 2013

(30) Foreign Application Priority Data
Dec. 23, 2010   (DE) .................. 20 2010 017 014 U

(51) Int. Cl.
| A61C 3/00 | (2006.01) |
|---|---|
| A61F 5/56 | (2006.01) |
| A61C 7/08 | (2006.01) |
| A61C 7/36 | (2006.01) |
| A61C 7/10 | (2006.01) |

(52) U.S. Cl.
CPC ... *A61C 7/08* (2013.01); *A61C 7/36* (2013.01); *A61F 5/566* (2013.01); *A61C 7/10* (2013.01)

(58) Field of Classification Search
CPC .............. A61C 7/08; A61C 7/36; A61C 7/10; A61F 5/566
USPC .......................................... 433/6, 19; 128/848
See application file for complete search history.

(56) References Cited

U.S. PATENT DOCUMENTS

| 5,409,017 | A | * | 4/1995 | Lowe ............................ 128/848 |
|---|---|---|---|---|
| 5,427,117 | A | * | 6/1995 | Thornton ...................... 128/848 |
| 5,829,441 | A | * | 11/1998 | Kidd et al. ................... 128/848 |
| 7,730,891 | B2 | * | 6/2010 | Lamberg ....................... 128/848 |
| 2003/0217753 | A1 | | 11/2003 | Thornton |

(Continued)

FOREIGN PATENT DOCUMENTS

| CN | 1476313 A | 2/2004 |
|---|---|---|
| DE | 20 2008 010 330 U1 | 10/2008 |
| DE | 20 2008 016 419 U1 | 2/2009 |
| WO | 02/26155 A2 | 4/2002 |

OTHER PUBLICATIONS

Translation of DE202008016419 retreived from http://worldwide.espacenet.com/publicationDetails/description?CC=DE&NR=202008016419U1&KC=U1&FT=D&ND=3&date=20090226&DB=worldwide.espacenet.com&locale=en_EP on Feb. 13, 2014.*

(Continued)

*Primary Examiner* — Heidi M Eide
(74) *Attorney, Agent, or Firm* — Craig Metcalf; Kirton McConkie

(57) ABSTRACT

The invention relates to an orthodontic apparatus that includes an upper jaw brace and a lower jaw brace. The braces each have an adjustment mechanism for an engaging part. The engaging parts engage together when the mouth is closed. Each adjustment mechanism has an adjustment spindle running in the sagittal direction of the jaw brace, the spindle head thereof can be accessed at the front by a tool. The position of the engaging part can thereby be adjusted very easily, and, among other things, also while the orthodontic apparatus is in the mouth of the patient.

11 Claims, 3 Drawing Sheets

(56) References Cited

U.S. PATENT DOCUMENTS

| | | | |
|---|---|---|---|
| 2005/0037312 A1* | 2/2005 | Uchida | 433/6 |
| 2006/0196512 A1 | 9/2006 | Gaskell | |
| 2007/0235037 A1* | 10/2007 | Thornton | 128/848 |
| 2008/0060659 A1* | 3/2008 | Bonato et al. | 128/848 |

OTHER PUBLICATIONS

Translation of DE 202008010330 retreived on Jan. 16, 2015 from WIOP http://patentscope.wipo.int/search/en/detail.jsf.*

* cited by examiner

ORTHODONTIC APPARATUS

This application is a National Stage of International Application No. PCT/EP2011/072644, filed Dec. 13, 2011, and entitled ORTHODONTIC APPARATUS, which claims the benefit of DE 20 2010 017 014.1, filed Dec. 23, 2010. This application claims priority to and incorporates herein by reference the above-referenced applications in their entirety.

The invention relates to an orthodontic apparatus comprising an upper jaw brace and a lower jaw brace, wherein at least one of these jaw braces has an engagement part adapted to be adjusted in the sagittal direction at the jaw brace by means of an adjustment mechanism.

An orthodontic apparatus from which the precharacterizing part of claim 1 starts is described in DE 20 2008 016 419 U (Köklü). This apparatus comprises an upper jaw brace and a lower jaw brace. Both jaw braces have engagement parts that cooperate when the mouth is closed, so as to correct the position of the lower jaw with respect to the upper jaw. Each of the two engagement parts may be adjustable at the associated jaw brace. However, it is sufficient if one of the engagement parts is adjustable, while the other is fixed on its jaw brace. In the known orthodontic apparatus, the adjustment mechanism of the one engagement part comprises a screwing device in the form of a Hyrax® screw. Such an adjustment device is situated entirely between the two legs of the respective jaw brace. For an adjustment of the engagement part, the jaw brace has to be taken out of the mouth. Thereafter, the spindle, which is provided with thread portions running in opposite directions, has to be turned by lateral application of a pin-shaped tool, the tool being inserted into transversal bores in the spindle. With such a structure, the spindle can be turned only section by section, each time covering only a limited angle of rotation. Thus, adjusting the engagement part at the jaw brace is tedious and time-consuming. Moreover, an adjustment inside the mouth of a patient is not possible so that the orthodontist cannot check the accuracy of fit of the respective adjustment in situ.

It is an object of the present invention to provide an orthodontic apparatus wherein the adjustment or regulation of the engagement part is simplified and which allows for a better and faster control by the orthodontist.

The orthodontic apparatus of the present invention is defined by claim 1. The adjustment spindle of the adjustment mechanism comprises a shaft end exposed at the frontal arch region of the jaw brace, where it has a coupling structure suited for the application of a turning tool from the front.

The orthodontic apparatus of the present invention thus significantly facilitates the adjustment and the control of the cooperating engagement parts of the upper jaw brace and the lower jaw brace. In particular, the adjustment procedure does not require the removal of either of the two jaw braces from the mouth of the patient, since the adjustment mechanism is accessible to the turning tool from the front, even if the engagement parts of both jaw braces are in mutual engagement. This allows for an in sit adjustment of the orthodontic apparatus, while it is possible during the adjustment procedure to ask the patient whether he feels pressure or other discomfort.

Preferably, the coupling structure is arranged sunken in the material of the jaw brace without protruding beyond the contour of this jaw brace. Thus, it is ensured that the comfort to the wearer is not compromised by protruding parts. Moreover, the coupling structure is arranged in a protected manner in the respective jaw brace.

Generally, the coupling structure is a hexagon socket or a square socket. This offers the advantage that a spindle head with a cylindrical outer surface can be used, wherein a gap between the spindle head and the plastic material of the jaw brace is reduced to zero.

The following is a detailed description of an embodiment of the invention with reference to the drawing.

Figure 1:
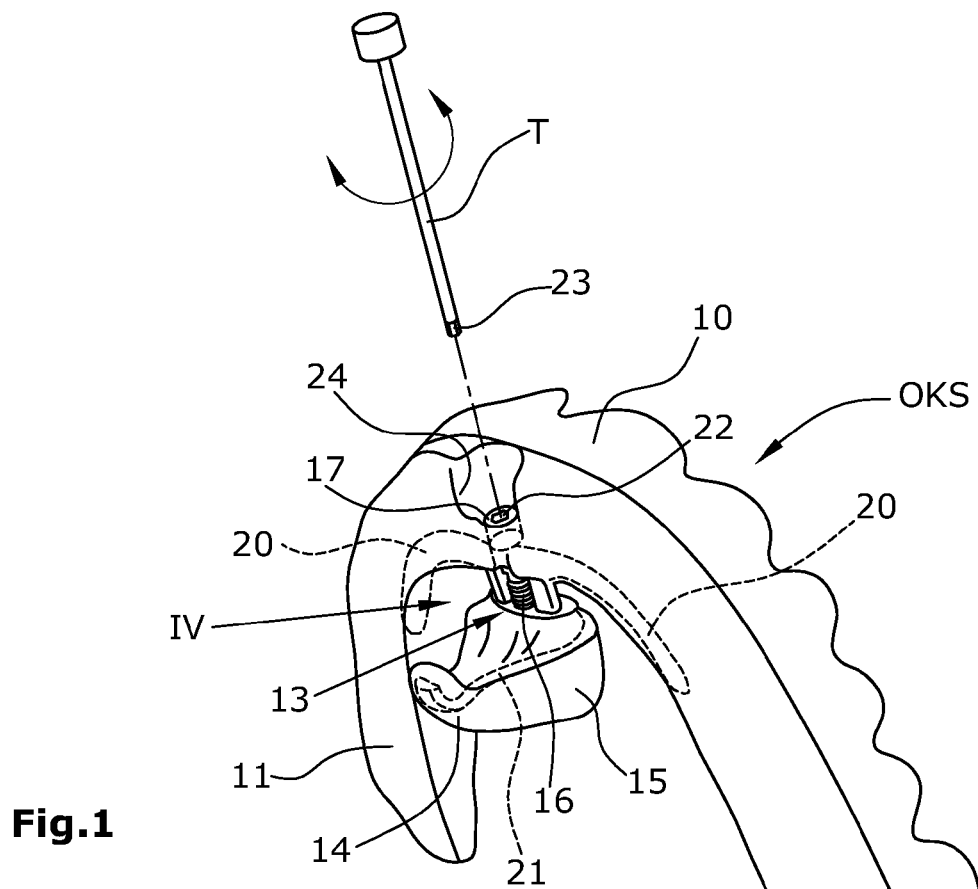
FIG. 1 is a perspective view of an upper jaw brace.

The orthodontic apparatus comprises an upper jaw brace OKS and a lower jaw brace UKS. Both braces are designed in the manner of dental brackets and therefore have substantially U-shaped basic shapes. In an impression-taking procedure, the braces are adapted to the shape of the jaws and the teeth of the patient so that they can be worn in the mouth of a patient without inconvenience and in a removable manner. The upper jaw brace OKS has a frontal arch region 10, as well as two lateral legs 11 and 12. The adjustment mechanism 13 protrudes from the rear of the arch region 10, the mechanism carrying a hook-shaped engagement part 14 whose center axis lies on the median plane of the jaw brace. The engagement part 14 is a part of a head member 15 of plastic material, whose position can be varied smoothly in the frontward (frontally) or rearward directions (dorsally) by actuation of the adjustment mechanism 13. A spindle nut (not illustrated) is provided in the head piece 15, which receives a screw-shaped spindle 16 that extends in the median plane of the jaw brace. At the front end of the spindle 16, a coupling structure 17 is situated to which a tool T can be applied to turn the spindle 16. Turning the spindle moves the engagement part 14 forward and backward.

The spindle nut supports two guide pins 18 protruding in parallel, the front ends thereof being connected by a yoke 19. The spindle head 17 forming the coupling structure is supported in the yoke 19. The yoke 19 is further connected with two arms 20 of flexible wire embedded in the synthetic resin material of the jaw brace. The arms cause an anchoring and an anti-rotation means for the adjustment mechanism 13 with respect to the jaw brace. The guide pins 18 pass into two arms 21 of flexible wire that are embedded in the synthetic resin material of the hook-shaped engagement part 14.

The adjustment mechanism 13 is a product of the company Forestadent.

As illustrated in FIG. 1, the spindle head forming the coupling structure 17 and comprising a hexagon socket 22 is accessible by frontal application of a tool T with an external hexagon 23. The tool T is applied in the longitudinal direction of the spindle 16 and is connected with the same in a manner fixed for rotation therewith, so as to turn the spindle 16 by turning the tool and to thereby displace the head element 15 with the engagement part 14. The spindle head is arranged in a recess 24 at the apex of the arch region 10. The spindle head has a cylindrical smooth outer surface so that it is embedded in the material of the jaw brace in a fitting and rotatable manner.

Figure 2:
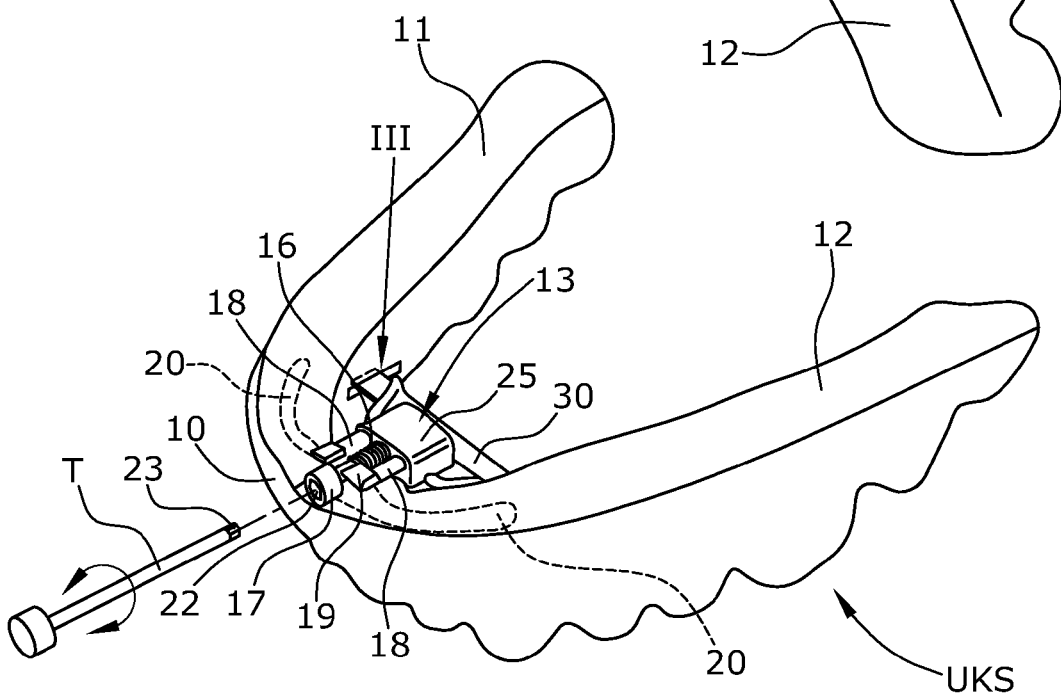
FIG. 2 is a perspective view of a lower jaw brace.
Figure 3:
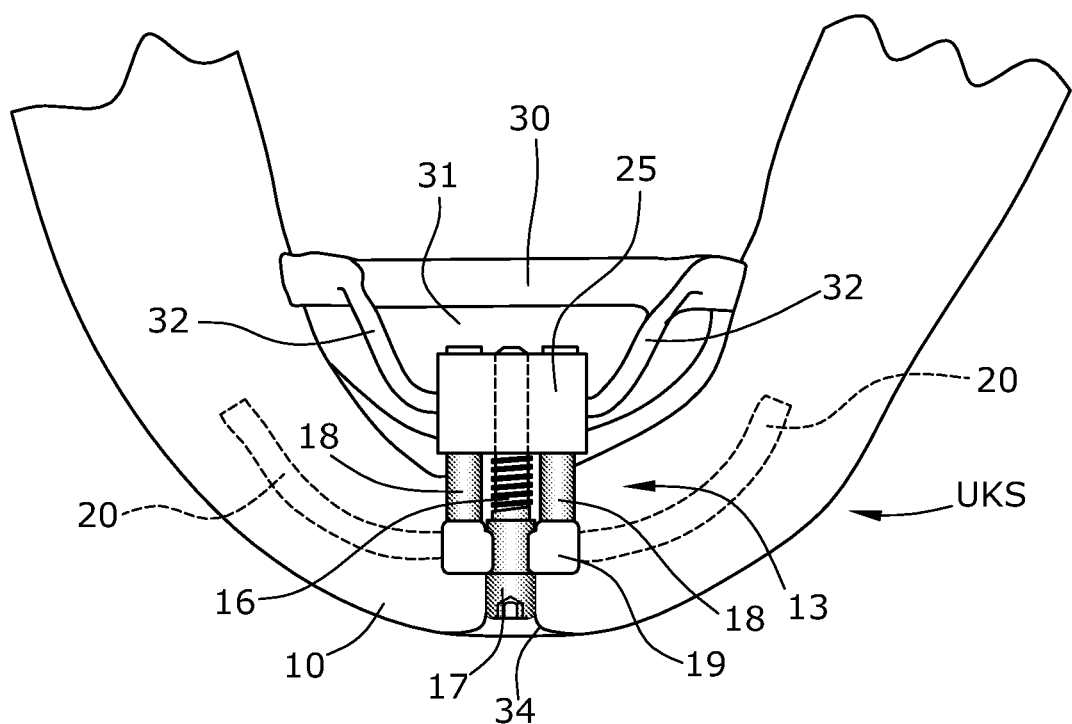
FIG. 3 is a top plan view on the lower jaw brace seen in the direction of the arrow III in FIG. 2.
Figure 4:
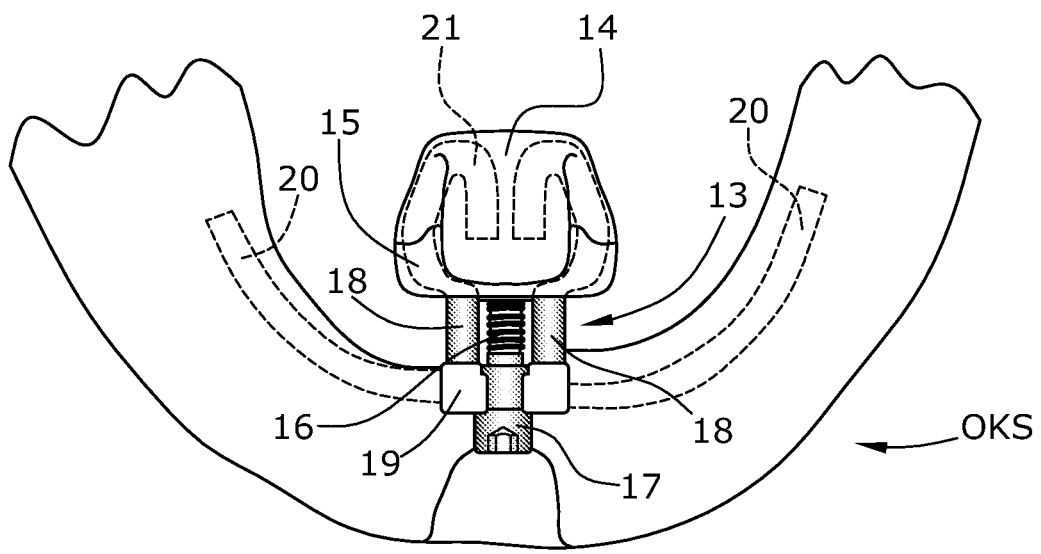
FIG. 4 is a top plan view on the upper jaw brace seen in the direction of the arrow IV in FIG. 1.

The lower jaw brace UKS illustrated in FIGS. 2 and 3 is configured in a manner similar to the upper jaw brace OKS. Here, the adjustment mechanism 13 is the same as with the upper jaw brace, the drawings (FIGS. 2 and 3) also illustrating the spindle nut 25 from which the two guide pins 18 project in a longitudinally displaceable manner. The spindle nut 25 protrudes dorsally from the arch region 10 and thus extends into the region between the lateral legs 11 and 12. An engagement part 30 in the form of a transverse bracket is connected with the spindle nut 25, the engagement part forming a loop 31 for passing therethrough the hook-shaped engagement part 14 of the upper jaw brace OKS. Arms 32 connect the transverse bracket 30 with the spindle nut 25. Also in this lower jaw brace, the yoke 19 is embedded in the material of the jaw brace, whereas the spindle nut with the engagement part attached thereto is displaceable in the longitudinal direction. The spindle head is situated in a recess 34 at the apex of the frontal arch region 10, where it is accessible by means of the tool T.

The engagement part 14 and the transversal bracket 30 together form an engagement mechanism which, when the mouth is closed, holds the upper jaw brace and the lower jaw brace together, while still allowing for sideward (lateral) relative movements.

In the present embodiment, both the upper jaw brace and the lower jaw brace are provided with an adjustment mechanism adapted to be actuated by applying a turning tool from the front. The cooperating engagement parts 14 and 30 of the two jaw braces can be adjusted separately while the respective jaw brace is in the patient's mouth.

Within the scope of the present invention, it is not necessary that both jaw braces are configured according to the invention. It is also possible that one jaw brace is provided with a different or no adjustment mechanism at all.

Figure 5:
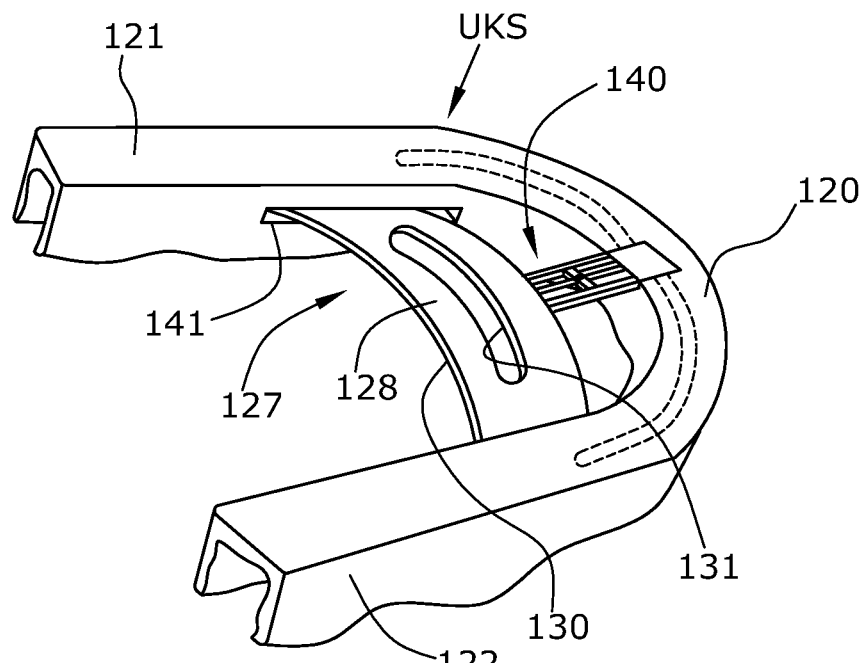
FIG. 5 is a perspective view of another embodiment of a lower jaw brace.

In the embodiment illustrated in FIG. 5, a lower jaw holder 127 is attached to the arch region 120 by means of a second screw device 140. It is basically configured in a manner similar to the first embodiment, i.e. with an elongate transversal ring 128 with a curvature 130 at the rear half of the ring for guiding an engagement part (web) 14 and with a curvature 130 at the front half of the ring. The lateral ends of the ring 128 are guided in guides 141 provided in the lateral legs 121, 122. In this embodiment, it is possible to adjust the upper jaw engagement part (web) in FIG. 1 in the sagittal direction by means of the adjustment mechanism 13 and to adjust the lower jaw holder 127 by means of the screw device 140.

Figure 6:
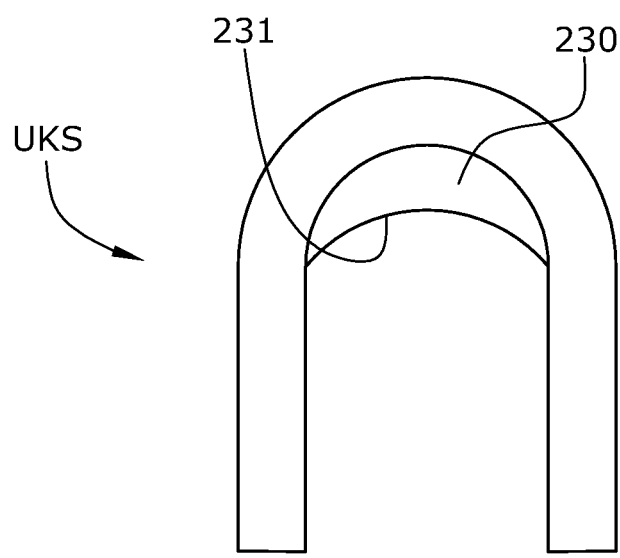
FIG. 6 is a perspective view of a further embodiment of a lower jaw brace.

The embodiment illustrated in FIG. 6 differs from the embodiment illustrated in FIG. 5 in that the engagement part 230 is not formed as an elongate transversal ring 128 with curvatures 130, 131, but rather as a plate in the lateral-sagittal plane. The hook-shaped engagement part 14 can engage the rear edge 231 of the plate 230. The plate is fixedly attached to the lower jaw brace and is not adjustable.

The invention claimed is:

1. An orthodontic apparatus comprising:
 a first jaw brace formed of a material that is shaped to fit overtop a wearer's teeth, the first jaw brace having a frontal arch region and two lateral legs that extend from opposite sides of the frontal arch region, the frontal arch region having an opening that is positioned at a median plane of the first jaw brace, the first jaw brace comprising:
  an engagement part spaced from the frontal arch region;
  a spindle nut secured within the engagement part;
  a yoke secured within the frontal arch region, the yoke having an opening that aligns with the opening in the frontal arch region;
  a spindle having a first end that inserts into the spindle nut and a second end that inserts through the opening in the yoke and into the opening in the frontal arch region;
  a spindle head connected to the second end of the spindle, the spindle head being positioned within the opening in the frontal arch region such that no portion of the spindle head extends beyond a front surface of the frontal arch region, the spindle head being configured to receive a tool for rotating the spindle head;
  two guide pins positioned on opposite sides of the spindle, each guide pin being connected between the yoke and the engagement part; and
  two arms that extend from opposite sides of the yoke, the arms being embedded within the lateral legs to provide support to prevent the yoke from rotating with respect to the frontal arch region;
  wherein, when the spindle head is rotated in a first direction, the spindle nut is moved along the spindle towards the yoke thereby causing the engagement part to be moved along the guide pins towards the yoke; and
 a second jaw brace formed of a material that is shaped to fit overtop a wearer's teeth, the second jaw brace having a frontal arch region and two lateral legs that extend from opposite sides of the frontal arch region, the second jaw brace comprising a second engagement part spaced from the frontal arch region of the second jaw brace to which the engagement part of the first jaw brace connects when the first and second jaw braces are worn;
 wherein the first jaw brace comprises an upper jaw brace and the second jaw brace comprises a lower jaw brace; and
 wherein the frontal arch region of the second jaw brace has an opening that is positioned at a median plane of the second jaw brace, the second jaw brace further comprising:
  a second spindle nut secured within the second engagement part;
  a second yoke secured within the frontal arch region of the second jaw brace, the second yoke having an opening that aligns with the opening in the frontal arch region of the second jaw brace;
  a second spindle having a first end that inserts into the second spindle nut and a second end that inserts through the opening in the second yoke and into the opening in the frontal arch region of the second jaw brace;
  a second spindle head connected to the second end of the second spindle, the second spindle head being positioned within the opening in the frontal arch region of the second jaw brace such that no portion of the second spindle head extends beyond a front surface of the frontal arch region of the second jaw brace, the second spindle head being configured to receive a tool for rotating the second spindle head;
  two second guide pins positioned on opposite sides of the second spindle, each second guide pin being connected between the second yoke and the second engagement part; and
  two second arms that extend from opposite sides of the second yoke, the second arms being embedded within the lateral legs of the second jaw brace to provide support to prevent the second yoke from rotating with respect to frontal arch region of the second jaw brace;
  wherein, when the second spindle head is rotated in a first direction, the second spindle nut is moved along the second spindle towards the second yoke thereby causing the second engagement part to be moved along the second guide pins towards the second yoke.

2. The orthodontic apparatus of claim 1, wherein the engagement part comprises a hook-shaped engagement part and the second engagement part comprises a transversal bracket to which the hook-shaped engagement part hooks.

3. The orthodontic apparatus of claim 1, wherein the spindle head comprises a hexagon socket.

4. The orthodontic apparatus of claim 1, wherein the engagement part comprises a synthetic resin.

5. The orthodontic apparatus of claim 1, wherein the opening in the frontal arch region has a diameter that increases towards the front surface of the frontal arch region.

6. An orthodontic apparatus comprising:
a first jaw brace and a second jaw brace that are each formed of a material that is shaped to fit overtop a wearer's teeth, each jaw brace having a frontal arch region and two lateral legs that extend from opposite sides of the frontal arch region, the frontal arch region having an opening that is positioned at a median plane of the jaw brace, each jaw brace comprising:
  an engagement part spaced from the frontal arch region;
  a spindle nut secured within the engagement part;
  a yoke secured within the frontal arch region, the yoke having an opening that aligns with the opening in the frontal arch region;
  a spindle having a first end that inserts into the spindle nut and a second end that inserts through the opening in the yoke and into the opening in the frontal arch region;
  a spindle head connected to the second end of the spindle, the spindle head being positioned within the opening in the frontal arch region such that no portion of the spindle head extends beyond a front surface of the frontal arch region, the spindle head being configured to receive a tool for rotating the spindle head;
  two guide pins positioned on opposite sides of the spindle, each guide pin being connected between the yoke and the engagement part; and
  two arms that extend from opposite sides of the yoke, the arms being embedded within the lateral legs to provide support to prevent the yoke from rotating with respect to the frontal arch region;
  wherein, when the spindle head is rotated in a first direction, the spindle nut is moved along the spindle towards the yoke thereby causing the engagement part to be moved along the guide pins towards the yoke.

7. The orthodontic apparatus of claim 6, wherein the first jaw brace is an upper jaw brace and the second jaw brace is a lower jaw brace.

8. The orthodontic apparatus of claim 6, wherein the engagement part of the first jaw brace comprises a hook-shaped engagement part that hooks onto the engagement part of the second jaw brace.

9. The orthodontic apparatus of claim 6, wherein the first jaw brace is a lower jaw brace and the second jaw brace is an upper jaw brace.

10. The orthodontic apparatus of claim 6, wherein the spindle head comprises a hexagon socket.

11. The orthodontic apparatus of claim 6, wherein the opening in the frontal arch region has a diameter that increases towards the front surface of the frontal arch region.

* * * * *